(12) United States Patent
Wulfman et al.

(10) Patent No.: US 10,959,869 B2
(45) Date of Patent: Mar. 30, 2021

(54) INTRODUCER WITH EXPANDABLE CAPABILITIES

(71) Applicant: BOSTON SCIENTIFIC SCIMED, INC., Maple Grove, MN (US)

(72) Inventors: David Robert Wulfman, Minneapolis, MN (US); Matthew Nelson Frost, Watertown, MN (US); Pieter Spitael, New Brighton, MN (US); Thomas Martin Keating, Galway (IE); Martyn G. Folan, Loughrea (IE); Martin Hynes, Galway (IE); Christopher Brian Rognrud, Blaine, MN (US); Matthew Boyer, Saint Louis Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 181 days.

(21) Appl. No.: 16/007,170

(22) Filed: Jun. 13, 2018

(65) Prior Publication Data
US 2018/0353312 A1 Dec. 13, 2018

Related U.S. Application Data

(60) Provisional application No. 62/518,843, filed on Jun. 13, 2017.

(51) Int. Cl.
*A61F 2/95* (2013.01)
*A61F 2/966* (2013.01)
(Continued)

(52) U.S. Cl.
CPC ................ *A61F 2/966* (2013.01); *A61F 2/86* (2013.01); *A61M 25/0662* (2013.01);
(Continued)

(58) Field of Classification Search
CPC .... A61F 2/86; A61F 2/966; A61F 2/95; A61F 2/958; A61F 2/07; A61F 2/962; A61F 2/954; A61F 2/06; A61F 2/24
See application file for complete search history.

(56) References Cited

U.S. PATENT DOCUMENTS

| 2006/0025749 A1 | 2/2006 | Moenning |
| 2009/0182411 A1* | 7/2009 | Irwin .................. A61F 2/97 623/1.12 |

(Continued)

FOREIGN PATENT DOCUMENTS

| EP | 2554141 A1 | 2/2013 |
| EP | 2995268 A1 | 3/2016 |

(Continued)

OTHER PUBLICATIONS

International Search Report and Written Opinion dated Sep. 20, 2018 for International Application No. PCT/US2018/037218.
(Continued)

*Primary Examiner* — Vi X Nguyen
(74) *Attorney, Agent, or Firm* — Seager, Tufte & Wickhem LLP

(57) ABSTRACT

An example introducer is disclosed. An example introducer sheath includes a tubular member including a first layer and a second layer and a stent disposed between the first layer and the second layer of the tubular member. The stent includes an outer surface and an inner surface. Additionally, the stent is configured to shift from a first configuration to a second expanded configuration and the outer surface of the stent contacts the first layer of the tubular member in the second expanded configuration.

8 Claims, 8 Drawing Sheets

(51) Int. Cl.
*A61F 2/86* (2013.01)
*A61M 25/06* (2006.01)
*A61M 25/00* (2006.01)
*A61M 25/01* (2006.01)

(52) U.S. Cl.
CPC .............. *A61F 2210/0004* (2013.01); *A61F 2210/0014* (2013.01); *A61F 2250/0098* (2013.01); *A61M 25/0068* (2013.01); *A61M 25/0074* (2013.01); *A61M 25/0119* (2013.01); *A61M 2025/0024* (2013.01)

(56) References Cited

U.S. PATENT DOCUMENTS

| 2014/0236122 A1 | 8/2014 | Anderson et al. |
| 2016/0074067 A1 | 3/2016 | Furnish et al. |
| 2016/0296332 A1 | 10/2016 | Zhou et al. |

FOREIGN PATENT DOCUMENTS

| JP | 2012040145 A | 3/2012 |
| WO | 2009035745 A1 | 3/2009 |
| WO | 2016164082 A1 | 10/2016 |

OTHER PUBLICATIONS

International Search Report and Written Opinion dated Mar. 8, 2018 for International Application No. PCT/US2017/065534.

\* cited by examiner

INTRODUCER WITH EXPANDABLE CAPABILITIES

CROSS-REFERENCE TO RELATED APPLICATIONS

This application claims the benefit of priority under 35 U.S.C. § 119 to U.S. Provisional Application Ser. No. 62/518,843, filed Jun. 13, 2017, the entirety of which is incorporated herein by reference.

TECHNICAL FIELD

The disclosure relates generally to medical devices and more particularly to medical devices that are adapted for use in percutaneous medical procedures.

BACKGROUND

In some instances, performing percutaneous medical procedures may require the insertion and/or maneuvering of relatively large medical devices through a patient's vasculature. However, inserting the medical device into the vasculature may result in undesirable forces being applied to the vessel walls. For example, as the medical device passes into the vasculature, it may make undesirable contact with one or more vessel walls. This interference may cause injury to the vessel as the medical device is navigated into calcified or diseased vessels. Therefore, in some instances an introducer is utilized to facilitate the insertion of medical devices into the vessel. Further, vessel trauma resulting from forces applied to the vessel wall by a medical device may be lessened by minimizing the size of an introducer used to access the vessel. Therefore, it may be desirable to design an introducer having a reduced insertion profile, yet capable of expansion when necessary (e.g., during the passage of a medical device therethrough).

SUMMARY

This disclosure provides design, material, manufacturing method, and use alternatives for medical devices. An example introducer sheath includes a tubular member including a first layer and a second layer and a stent disposed between the first layer and the second layer of the tubular member. The stent includes an outer surface and an inner surface. Additionally, the stent is configured to shift from a first configuration to a second expanded configuration and the outer surface of the stent contacts the first layer of the tubular member in the second expanded configuration.

Alternatively or additionally to any of the embodiments above, wherein the stent is slidable relative to the first layer and second layer of the tubular member.

Alternatively or additionally to any of the embodiments above, wherein the stent is designed to foreshorten, and wherein foreshortening the stent shifts the stent from the first configuration to the second expanded configuration.

Alternatively or additionally to any of the embodiments above, wherein the stent includes a proximal end, and wherein shifting the proximal end in a distal direction shifts the stent from the first configuration to the second expanded configuration.

Alternatively or additionally to any of the embodiments above, wherein the first layer of tubular member is radially outward of the second layer of the tubular member.

Alternatively or additionally to any of the embodiments above, wherein the first layer of the tubular member is continuous with the second layer of the tubular member.

Alternatively or additionally to any of the embodiments above, wherein the second layer of the tubular member folds back on itself to form the first layer of the tubular member.

Alternatively or additionally to any of the embodiments above, wherein the tubular member further comprises a lumen extending therein, and wherein the lumen is positioned radially inward of both the first layer and the second layer.

Alternatively or additionally to any of the embodiments above, wherein the tubular member includes a first length in the first configuration and a second length in the expanded configuration, and wherein the first length is substantially the same as the second length.

Alternatively or additionally to any of the embodiments above, wherein the tubular member includes a first outer diameter in the first configuration and a second outer diameter in the expanded configuration, and wherein the first outer diameter is less than the second outer diameter.

Another introducer sheath includes:
 a tubular member having a first layer and a second layer;
 an expandable member disposed between the first layer and the second layer;
 wherein the tubular member is designed to shift between a first elongated configuration and a second expanded and foreshortened configuration;
 wherein shifting the tubular member to the second configuration includes expanding the expandable member.

Alternatively or additionally to any of the embodiments above, wherein the expandable member is slidable relative to the first layer and second layer of the tubular member.

Alternatively or additionally to any of the embodiments above, wherein the expandable member is designed to foreshorten, and wherein foreshortening the expandable member shifts the expandable member from the first configuration to the second expanded configuration.

Alternatively or additionally to any of the embodiments above, wherein the first layer of tubular member is radially outward of the second layer of the tubular member.

Alternatively or additionally to any of the embodiments above, wherein the tubular member includes a proximal end, and wherein shifting the proximal end in a proximal direction shifts the stent from the first configuration to the second expanded configuration.

Alternatively or additionally to any of the embodiments above, wherein the first layer of the tubular member is continuous with the second layer of the tubular member.

Alternatively or additionally to any of the embodiments above, wherein the second layer of the tubular member folds back on itself to form the first layer of the tubular member.

Alternatively or additionally to any of the embodiments above, wherein the tubular member further comprises a lumen extending therein, and wherein the lumen is positioned radially inward of both the first layer and the second layer.

A method of inserting a medical device into a body includes:
 positioning an introducer sheath within a body lumen, the introducer sheath including:
  a tubular member including a first layer and a second layer; and
  a stent disposed between the first layer and the second layer of the tubular member, the stent including an outer surface and an inner surface;

advancing a medical device through the introducer sheath, wherein advancing the medical device through the introducer sheath shifts the tubular member between a first configuration and a second expanded configuration, and wherein shifting the tubular member to the second configuration includes expanding the stent.

Alternatively or additionally to any of the embodiments above, wherein the stent is slidable relative to the first layer and second layer of the tubular member.

The above summary of some examples is not intended to describe each disclosed embodiment or every implementation of the present disclosure. The Figures, and Detailed Description, which follow, more particularly exemplify these examples.

Figure 1:
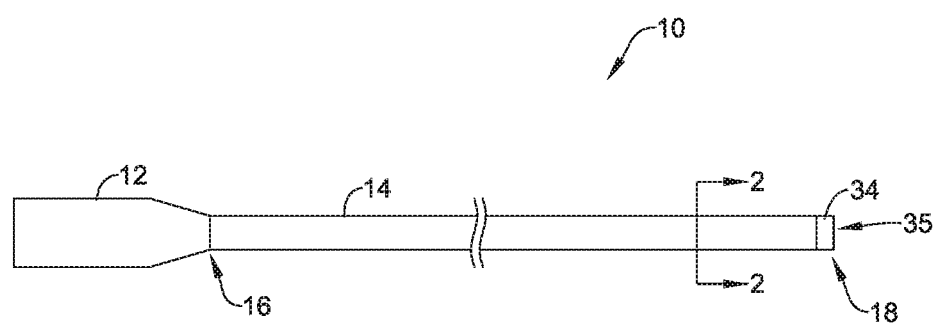
FIG. 1 is a plan view of an example introducer.

While the disclosure is amenable to various modifications and alternative forms, specifics thereof have been shown by way of example in the drawings and will be described in detail. It should be understood, however, that the intention is not to limit the disclosure to the particular examples described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some examples", "other examples", etc., indicate that the embodiment described may include one or more particular features, structures, and/or characteristics. However, such recitations do not necessarily mean that all examples include the particular features, structures, and/or characteristics. Additionally, when particular features, structures, and/or characteristics are described in connection with one embodiment, it should be understood that such features, structures, and/or characteristics may also be used connection with other examples whether or not explicitly described unless clearly stated to the contrary.

The following detailed description should be read with reference to the drawings in which similar elements in different drawings are numbered the same. The drawings, which are not necessarily to scale, depict illustrative examples and are not intended to limit the scope of the disclosure.

In some instances, performing percutaneous medical procedures may require the insertion and/or maneuvering of relatively large medical devices through a patient's vasculature. However, inserting the medical device into the vasculature may result in undesirable forces being applied to the vessel walls. For example, as the medical device passes into the vasculature, it may make undesirable contact with one or more vessel walls. This interference may cause injury to the vessel as the medical device is navigated into calcified or diseased vessels. Therefore, in some instances an introducer is utilized to facilitate the insertion of medical devices into the vessel. Further, vessel trauma resulting from forces applied to the vessel wall by a medical device may be lessened by minimizing the size of an introducer used to access the vessel. Therefore, it may be desirable to design an introducer having a reduced insertion profile, yet capable of expansion when necessary (e.g., during the passage of a medical device therethrough). The following examples disclose an intravascular medical device including an expandable introducer, whereby the introducer is designed to expand from a reduced profile, unexpanded configuration to an expanded configuration.

FIG. 1 illustrates an example expandable introducer (e.g., delivery sheath, access sheath, etc.) 10. The introducer 10 may include a tubular member 14. The tubular member 14 may include a proximal end region 16 and a distal end region 18. The tubular member 14 may further include a lumen 35 extending therethrough (discussed in greater detail below). The tubular member 14 may be constructed from a lubricious polymer fiber. For example, the tubular member 14 may be constructed from a composite of fluoropolymer (e.g., PVDF-HFP) fiber and silicone. This composition may have the advantage of making the tubular member 14 tough, thin and lubricious.

Further, the introducer 10 may include a manifold 12. The proximal end region 16 of the tubular member may be attached to the manifold 12. Additionally, the manifold 12 may include a hemostatic valve or seal disposed therein. The hemostatic valve or seal may prevent blood or other bodily fluid(s) from flowing proximally through the lumen 35 of the tubular member 14. In at least some examples, the manifold 12 may include a port (not shown) in fluid communication with the lumen 35 of the tubular member 14.

In some examples it may be desirable to add a tip member 34 to the distal end of any of the examples disclosed herein. The tip member 34 may be designed with a low durometer material. In some instances, a lower durometer material may provide the tip member 34 with the ability to radially expand (e.g., flex) outward and radially contract as a variety of medical devices are advanced through the tip member 34. Further, the tip member 34 may include a taper. For example, the tip member 34 may taper from a first diameter to a second diameter at the distal end of the introducer 10. While not intended to be limiting, in some examples the shape of the tip member 34 may resemble a bull-nose. Additionally, the tip member 34 may include a radiopaque material. The radiopaque material may allow the tip member 34 to be visualized by a clinician during a medical procedure. In some examples, the tip member 34 may be segmented radially and/or dissected such that it may separate into segments upon expansion. While it is contemplated that any of the examples described herein may include a tip member, this is not intended to be limiting. Rather, as shown in the figures, some examples described herein do not include a tip member.

Figure 2:
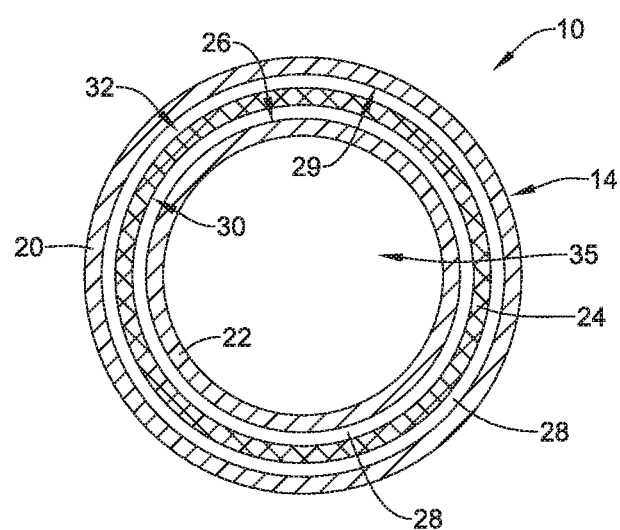
FIG. 2 is a cross-sectional view along line 2-2 of the introducer shown in FIG. 1.

FIG. 2 is a cross-sectional view of the introducer 10 taken along line 2-2 of FIG. 1. As shown in FIG. 2, in some examples the tubular member 14 may include a second layer 22 and a first layer 20. In some examples, the second layer 22 of the tubular member 14 may be referred to as an inner layer. Similarly, in some examples, the first layer 20 of the tubular member 14 may be referred to as an outer layer. It can be appreciated from FIG. 2 that the first layer 20 is positioned radially outward (e.g., radially away from) the second layer 22. FIG. 2 also illustrates the lumen 35 described above with respect to FIG. 1. As illustrated in FIG. 2, the lumen 35 may be positioned radially inward of the second layer 22, the first layer 20 or both the second layer 22 and the first layer 20.

As will be described in greater detail below, FIG. 2 illustrates that the introducer 10 may include a space 28 (e.g., gap, void, etc.) that is located between the second layer 22 and the first layer 20. In other words, the space 28 may be defined as the absence of material extending between the outer surface 26 of the second layer 22 (as it is depicted in FIG. 2) and the inner surface 29 of the first layer 20 (as it is depicted in FIG. 2).

Further, FIG. 2 illustrates that in some examples, the introducer 10 may include an expandable member 24 (e.g., stent) disposed in the space 28 (described above). The expandable member 24 may include an inner surface 30 and an outer surface 32. As shown in FIG. 2, the inner surface 30 and/or the outer surface 32 of the expandable member 24 may not contact the outer surface 26 of the second layer 22 and/or the inner surface 29 of the first layer 20. However, this is not intended to be limiting. Rather, in some examples the inner surface 30 and/or the outer surface 32 of the expandable member 24 may not contact the outer surface 26 of the second layer 22 and/or the inner surface 29 of the first layer 20. In some examples, the tubular member 14 may be sized such that its diameter is smaller than the stent diameter when fully compressed.

In some instances, the expandable member 24 may be a self-expanding stent. Self-expanding stent examples may include an expandable framework having one or more filaments combined to form a rigid and/or semi-rigid stent structure. For example, stent filaments may be braided, intertwined, interwoven, woven, knitted or the like to form an expandable frame.

The expandable member 24 in the examples disclosed herein may be constructed from a variety of materials. For example, the expandable member 24 may be constructed from a metal (e.g., Nitinol). In other instances, the expandable member 24 may be constructed from a polymeric material (e.g., PET). In yet other instances, the expandable member 24 may be constructed from a combination of metallic and polymeric materials. Additionally, the expandable member 24 may include a bioabsorbable and/or biodegradable material.

Figure 3:
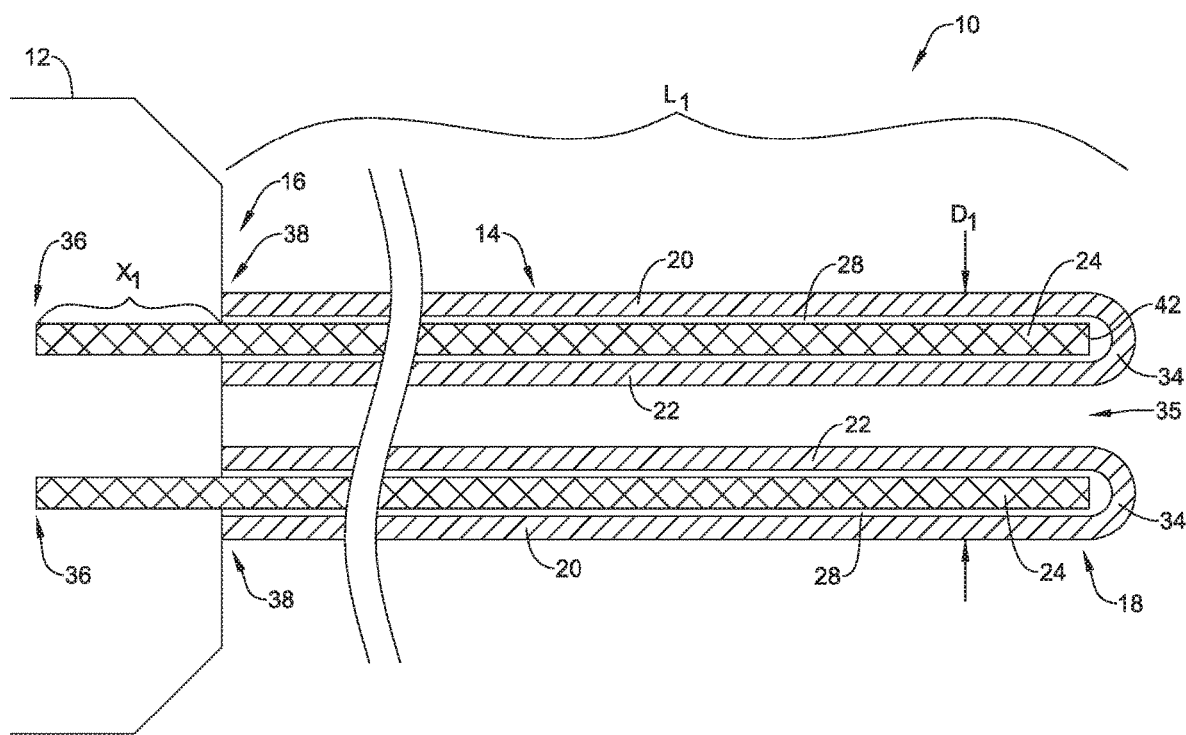
FIG. 3 is a partial cross-sectional view of the introducer shown in FIG. 1.

FIG. 3 illustrates a partial cross-sectional view of the introducer 10 described above including the second layer 22, first layer 20 and the expandable member 24 disposed within the space 28 between the second layer 22 and first layer 20. It can be appreciated that FIG. 3 may depict the introducer 10 in an unexpanded (e.g., compressed) configuration. As compared to an expanded configuration (discussed below), introducer 10 in a compressed configuration may be compressible in the axial direction, more compliant, and more radially compliant. It can be further appreciated that in the unexpanded configuration, the introducer 10 may include an outer diameter depicted as "$D_1$" in FIG. 3. Additionally, FIG. 3 illustrates that the tubular member 14 may have a length depicted as "$L_1$" in the unexpanded configuration.

FIG. 3 shows that in at least some examples, the proximal end region 16 of the tubular member may be coupled (e.g., attached, affixed, disposed along, etc.) to a portion of the manifold 12 (described and shown above in FIG. 1). For example, FIG. 3 illustrates that in some examples the tubular member may be coupled to the manifold at one or more fixation points 38. Additionally, FIG. 3 shows that in some examples, that the proximal end region 16 of the tubular member may include the proximal ends of both the first layer 20 and the second layer 22 of the tubular member 14.

While FIG. 3 shows that the proximal end region 16 of the tubular member (including the proximal ends of both the first layer 20 and the second layer 22 of the tubular member 14) attached to the manifold 12 at fixation points 38, this is not intended to be limiting. Rather, it is contemplated that in some instances, the proximal end region 16 of the tubular member may be disposed, affixed, attached, etc. to any portion of the manifold 12. For example, it is contemplated that a portion of the proximal end region 16 of the tubular member 14 may extend into the manifold 12. Other examples contemplate that the tubular member 14 and manifold 12 may be coupled together via a secondary member (e.g., a collar, coupling member, etc.).

As discussed above, with respect to FIG. 1, the introducer 10 may include a tip member 34 disposed along the distal end region 18 of tubular member 14. However, FIG. 3 shows another example in which the distal tip 34 of the introducer 10 may be formed from the tubular member. Specifically, FIG. 3 illustrates that in at least one example contemplated here, the second layer 22 of the tubular member may "fold back" on itself to form the first layer 20 of the tubular member 14. In other words, the tubular member 14 may be characterized as an "inverted tube" whereby the first layer 20 and the second layer 22 are formed from a monolithic tube which has been inverted on itself to form an inner layer and an outer layer. As can be appreciated from FIG. 3, the distal tip 34 of the tubular member 14 described above (and illustrated in FIG. 3) would include the curved portion whereby the second layer 22 "transitions" to the first layer 20.

FIG. 3 further illustrates expandable member 24 disposed within the space 28 between the second layer 22 and the first layer 20 of the tubular member 14. It can be appreciated that in at least some examples, the expandable member 24 may be slidingly disposed between the second layer 22 and the first layer 20. In other words, in at least some examples, the expandable member 24 may be able to slide (e.g., move, shift, etc.) relative to the second layer 22 and/or the first layer 20.

Additionally, FIG. 3 illustrates that in some examples, a proximal end 36 of the expandable member 24 may extend into a portion of the manifold 12. FIG. 3 further illustrates that the expandable member 24 may extend into the manifold a distance depicted as "$X_1$." As will be discussed in greater detail below, in some examples the proximal end 36 of the expandable member 24 may be configured to shift in a proximal-to-distal direction. In other words, the proximal end 36 of the expandable member 24 may not be fixed relative to the manifold 12 and may be able to move relative thereto.

FIG. 3 further illustrates that the distal end 42 of the expandable member 24 may be positioned adjacent the distal end of the tubular member 14. As shown in FIG. 3, the distal end 42 of the expandable member 24 may extend within space 28 such that it is adjacent the distal end of the tubular member 14. In some examples, the distal end 42 of the expandable member 24 may abut (e.g., contact, touch, etc.) the tubular member 14.

Figure 4:
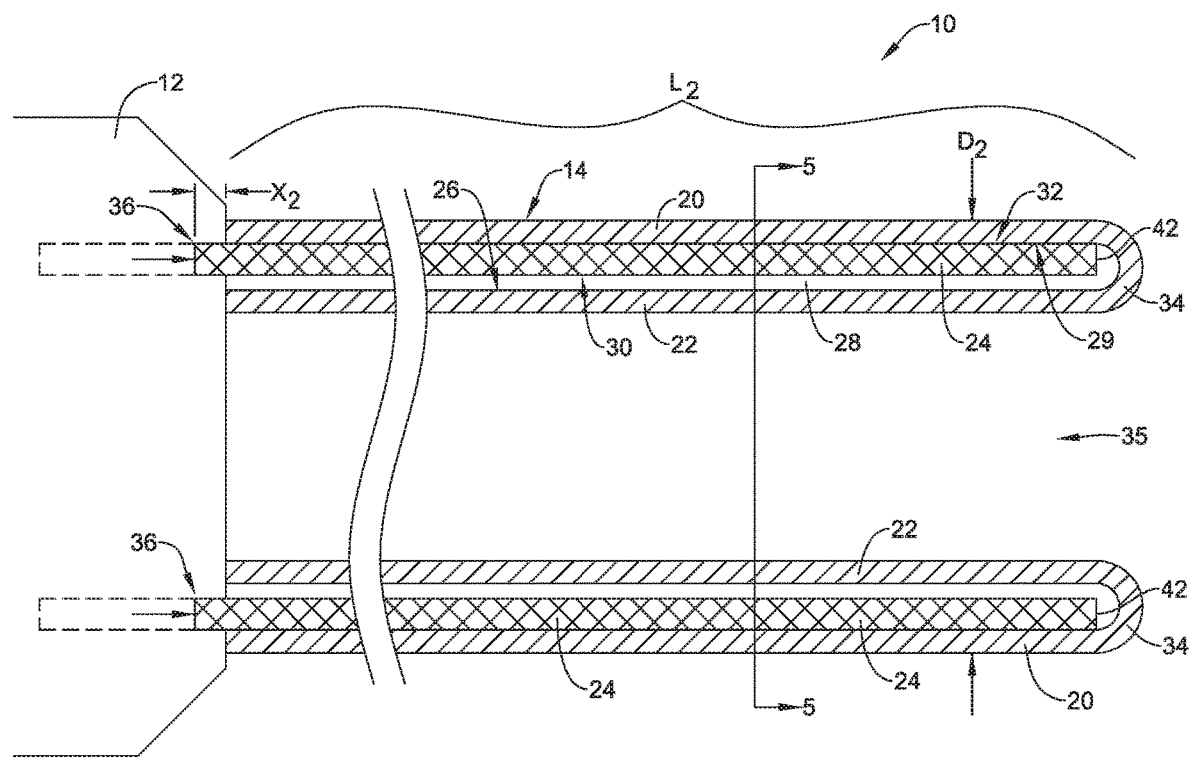
FIG. 4 is a partial cross-sectional view of the introducer shown in FIG. 1 in an expanded configuration.

FIG. 4 illustrates that introducer 10 shown in FIG. 3 in an expanded configuration. It can be further appreciated that in the expanded configuration, the introducer 10 may include an outer diameter depicted as "$D_2$" in FIG. 4. Diameter $D_2$ may be larger than the unexpanded diameter $D_1$ illustrated in FIG. 3. For example, diameter $D_2$ may be about 1 to 10 times larger than the unexpanded diameter $D_1$, or about 1 to 5 times larger than the unexpanded diameter $D_1$, or about 1 to 2.5 times larger than the unexpanded diameter $D_1$. These are just examples, other expansion ratios are contemplated. For example, in some instances the expansion ratios may be adjusted up or down based on the design of the expandable member, as will be discussed in greater detail below.

FIG. 4 further illustrates that in some examples, the tubular member 14 may be expanded via the outward, radial expansion of the expandable member 24. In other words, expanding the expandable member 24 radially outward may result in the outer surface 32 (shown in FIG. 1 and FIG. 4) of the expandable member 24 to contact the inner surface 29 (shown in FIG. 1 and FIG. 4) of the first layer 20, thereby radially expanding the tubular member 14 outward. For example, FIG. 4 illustrates the outer surface 32 (shown in FIG. 1 and FIG. 4) of the expandable member 24 contacting the inner surface 29 (shown in FIG. 1 and FIG. 4) of the first layer 20. However, FIG. 4 also illustrates that the inner surface 30 (shown in FIG. 1 and FIG. 4) of the expandable member 24 may not contact the outer surface 26 (shown in FIG. 1 and FIG. 4) of the second layer 22 of the tubular member. Therefore, in some examples, a gap 28 may still exist between the inner surface 30 of the expandable member 24 and the outer surface 26 of the second layer 22. However, this is not intended to be limiting. Rather, in some examples the inner surface 30 of the expandable member 24 may contact the outer surface 26 of the second layer 22 upon expansion of the expandable member 24.

FIG. 4 further illustrates that, in some examples, the tubular member 14 may be designed to expand radially outward while its length remains constant. For example, it can be appreciated that, as illustrated and described with respect to FIG. 3, if the proximal end region 16 of the tubular member 14 is fixed (e.g., at fixation points 38) with respect to the manifold 12 and the tubular member 14 is prevented from lengthening along its longitudinal axis (e.g., by utilizing a particular material or structural design), radial expansion of the expandable member 24 may translate into radial expansion of the tubular member 14 without lengthening the tubular member longitudinally. For example, FIG. 4 shows the length of the tubular member in the expanded configuration as "$L_2$." In some examples, the length $L_1$ of the tubular member in an unexpanded configuration (shown in FIG. 3) may be substantially equivalent to the length $L_2$ of the tubular member in an expanded configuration (shown in FIG. 4).

FIG. 4 further illustrates the expansion of the expandable member 24 radially outward. As shown in FIG. 4 and discussed above, the proximal end 36 of the expandable member 24 may extend into and move relative to the manifold 12. It can be further appreciated, therefore, that the manifold 12 may be designed to permit the proximal end 36 of the expandable member 24 to be shifted in a proximal-to-distal direction (as depicted by the arrows in FIG. 4). In other words, it can be appreciated that the manifold 12 may be designed with one or more components (not shown for simplicity purposes) that can exert a force on the proximal end 36 of the expandable member 24 such that the proximal end 36 of the expandable member 24 may shift in a proximal-to-distal direction (as depicted by the arrows in FIG. 4). For example, FIG. 3 illustrates the proximal end 36 of the expandable member 24 extending a distance depicted as "$X_1$" into the manifold 12 (in the unexpanded configuration), while FIG. 4 depicts the proximal end 36 of the manifold extending a distance depicted as "$X_2$" into the manifold 12 (in the expanded configuration), wherein distance "$X_1$" is greater than distance "$X_2$." Further, as discussed above, in some examples (such as that described in FIG. 3 and FIG. 4), the distal end 42 of the expandable member 24 may be held stationary via the tubular member (which, as discussed above) may be designed to resist lengthening in the longitudinal direction. Consequently, it can be appreciated that if the proximal end 36 of the expandable member 24 is shifted in a proximal-to-distal direction while the distal end 42 of the expandable member is held stationary, then the expandable member 24 (and, consequently, the tubular member 14) may expand radially outward, as discussed above.

Additionally, it can further be appreciated that in the expanded configuration shown in FIG. 4, the expandable member 24, together with the tubular member 14, may offer a balance of structure and lubricity to translate a medical device through the lumen 35 of the introducer 10. For example, the tubular member 14 may provide a surface texture, lubricity, etc. that reduces the frictional forces of a medical device translating through the lumen 35 of the introducer 10, while the expandable member 24 provides sufficient radial support (e.g. hoop strength) against the vessel wall to permit efficient translation of a medical device therethrough.

It is contemplated that for at least some of the examples disclosed herein, the particular design characteristics of the expandable component 24 may control the minimum and maximum expansion ratios of the introducer 10. For example, the expandable component 24 may be "tuned" and optimized for the specific needs and intended use of the introducer sheath 10. For example, the expandable component 24 may be designed from a particular material, have particular thickness, length and diameter dimensions which tailor the expansion characteristics of the introducer sheath.

Further, the tubular member 14 may be designed to cooperate with the design of the expandable component 24. For example, the tubular member 14 may provide a balance between allowing the expandable member 24 to freely expand to a desired diameter while also limiting the expandable member 24 from expanding to an undesirable diameter. Additionally, it is contemplated that in some examples, the action of the tubular member 14 resisting expansion of the expandable member 24 causes the introducer sheath 10 to become a more rigid structure. In other words, as the expandable member 24 expands radially outward (via a shortening of the expandable member 24, as described above), it eventually contacts the inner surface of the tubular member 14, whereby the tubular member 14 begins to both expand and also resist further expansion of the tubular member 24. The tubular member's 14 resistance to expansion manifests in a more rigid introducer 10 (e.g., the combination of the tubular member 14 and expandable member 24 becomes more rigid). A more rigid introducer 10 may be less likely to buckle as medical devices are passed therethrough. In some examples, the interaction between the tubular member 14 and the expandable member 24 provides a limit to the extent the expandable member 24 is permitted to expand, which may provide a degree of protection against injury to the vessel wall. It is contemplated that the interaction described between the tubular member 14 and the expandable member 24 described above may be applicable to any of the introducer examples disclosed herein.

FIG. 3 and FIG. 4 are schematic illustrations of an example introducer sheath shifting from an unexpanded configuration to and expanded configuration. The particular design of the components relative thereto are not intended to be limiting. For example, it is contemplated that the manifold 12 and components thereof may be designed in a variety of ways to attach to the tubular member 14 and provide a force to the proximal end 36 of the expandable member 24. Further, additional configurations, designs and engagement of the tubular member 14 and the expandable member 24 with a distal end region of the manifold 12 are contemplated. It can be appreciated that a variety of different manifold configurations may permit the tubular member 14 and the expandable member 24 to function as described herein.

Figure 5:
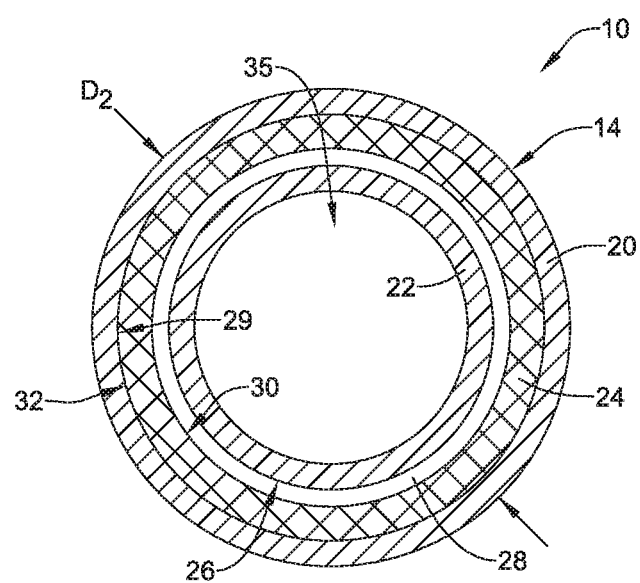
FIG. 5 is a cross-sectional view along line 5-5 of the introducer shown in FIG. 4.

FIG. 5 is a cross-sectional view of the introducer 10 taken along line 5-5 of FIG. 4. FIG. 5 illustrates the tubular member 14 including a second layer 22, first layer 20 and the expandable member 24 disposed within the space 28 between the second layer 22 and first layer 20. It can be appreciated that FIG. 5 may depict the introducer 10 in an expanded configuration. It can be further appreciated that in the expanded configuration, the introducer 10 may include an outer diameter depicted as "$D_2$" in FIG. 5. As discussed above, FIG. 5 illustrates the outer surface 32 of the expandable member 24 contacting the inner surface 29 of the first layer 20. However, FIG. 5 also illustrates that the inner surface 30 of the expandable member 24 may not contact the outer surface 26 of the second layer 22 of the tubular member. Therefore, in some examples, a gap 28 may still exist between the inner surface 30 of the expandable member 24 and the outer surface 26 of the second layer 22.

Figure 6:
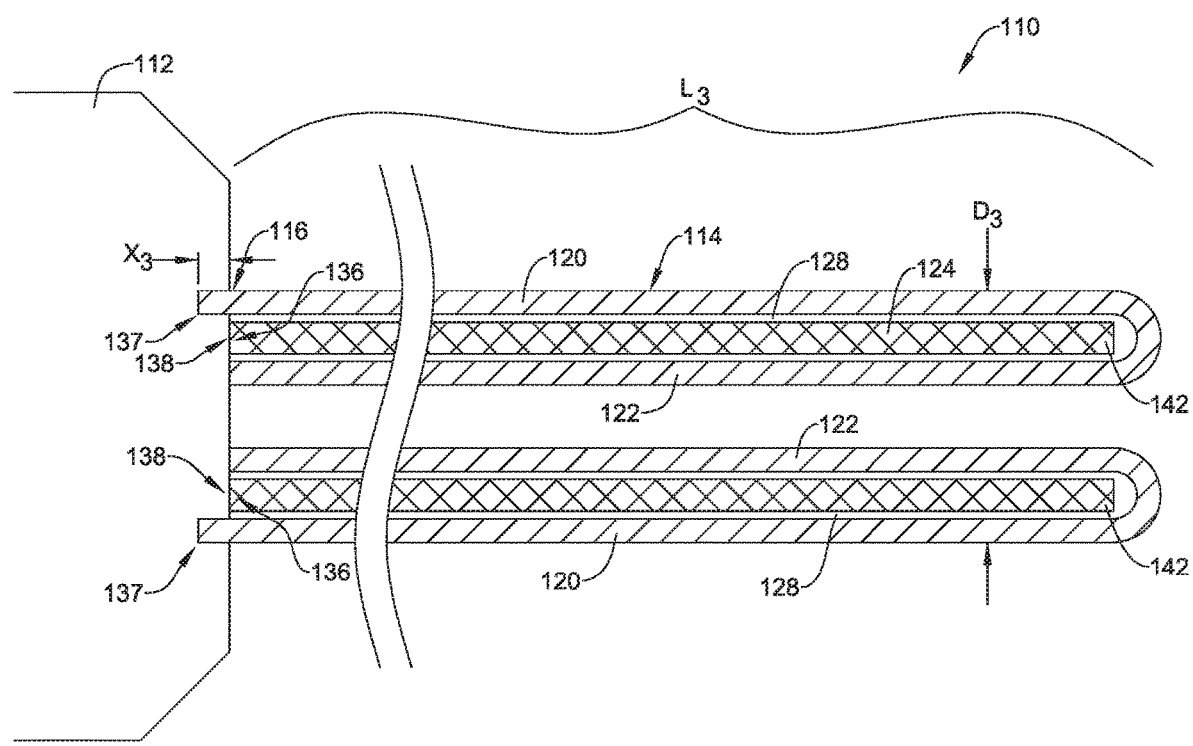
FIG. 6 is a partial cross-sectional view of another example introducer.
Figure 7:
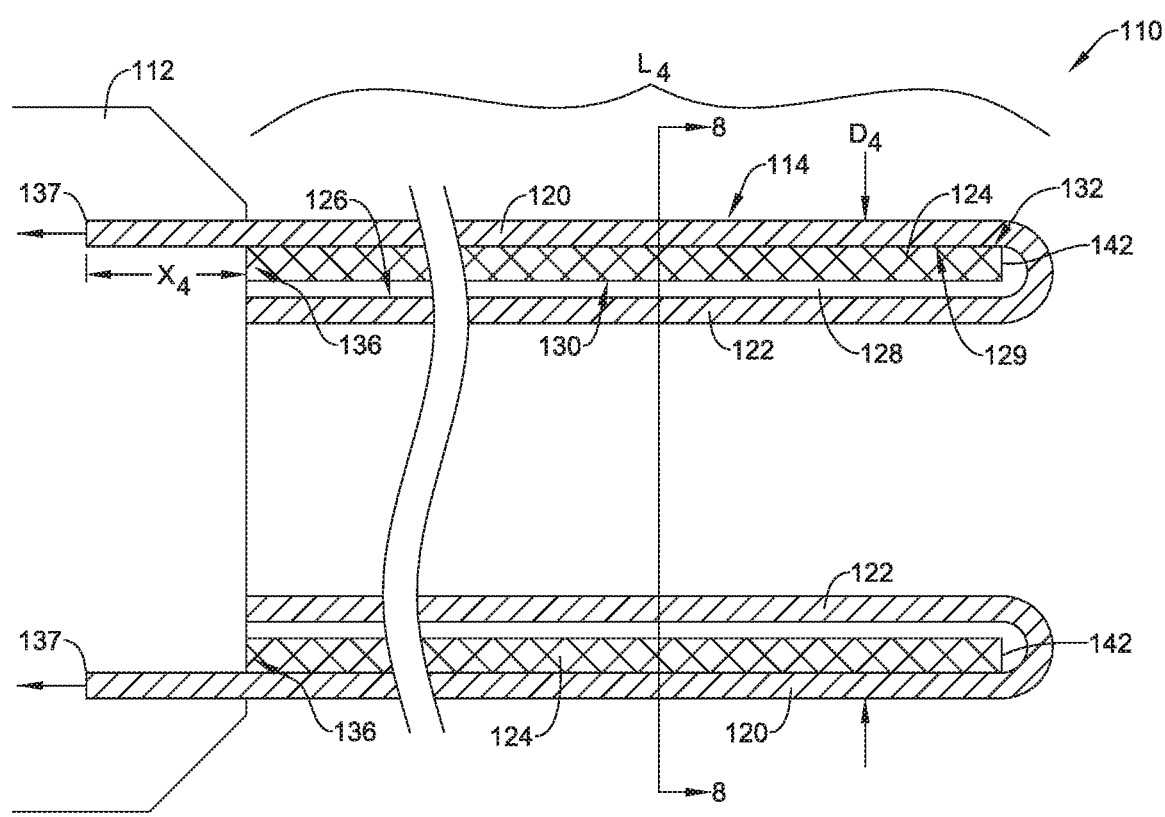
FIG. 7 is a partial cross-sectional view of the introducer shown in FIG. 6 in an expanded configuration.

FIG. 6 and FIG. 7 illustrate another example expandable introducer sheath 110. The expandable introducer sheath 110 may be similar in form and function to other example introducer sheaths described herein. For example, the introducer sheath 110 (and components thereof) may be similar in form and function to the introducer 10 described above.

FIG. 6 shows the introducer sheath 110 including a tubular member 114. The tubular member 114 may include a second layer 122, a first layer 120 and an expandable member 124 positioned within a gap 128. Additionally, FIG. 6 illustrates that the proximal end 136 of the expandable member 124 may be coupled (e.g., attached, secured, fixed, etc.) to a distal region of the manifold 112 at fixation points 138. Additionally, FIG. 6 illustrates that the tubular member 14 may have a length depicted as "$L_3$" in the unexpanded configuration.

Additionally, FIG. 6 illustrates that in some examples, a proximal end 137 of the tubular member 114 may extend into a portion of the manifold 112. For example, FIG. 6 illustrates that a portion of the first layer 120 of the tubular member 114 may extend into the manifold 112 a distance depicted as "$X_3$." As will be discussed in greater detail below, in some examples the proximal end 137 of the tubular member 114 may be configured shift in a distal-to-proximal direction. In other words, the proximal end 137 of the tubular member 114 may not be fixed relative to the manifold 112 and may be able to move relative thereto.

FIG. 6 further illustrates that the distal end 142 of the expandable member 124 may be positioned adjacent the distal end of the tubular member 114. As shown in FIG. 6, the distal end 142 of the expandable member 124 may extend within the space 128 such that it is adjacent the distal end of the tubular member 114. In some examples, the distal end 142 of the expandable member 124 may abut (e.g., contact, touch, etc.) the tubular member 114.

FIG. 7 illustrates that introducer 110 shown in FIG. 6 in an expanded configuration. It can be further appreciated that in the expanded configuration, the introducer 110 may include an outer diameter depicted as "$D_4$" in FIG. 6. Diameter $D_4$ may be larger than the unexpanded diameter $D_3$ illustrated in FIG. 6. For example, diameter $D_4$ may be about 1 to 10 times larger than the unexpanded diameter $D_3$, or about 1 to 5 times larger than the unexpanded diameter $D_3$, or about 1 to 2.5 times larger than the unexpanded diameter $D_3$. These are just examples, other expansion ratios are contemplated. For example, in some instances the expansion ratios may be adjusted up or down based on the design of the expandable member, as will be discussed in greater detail below.

FIG. 7 further illustrates that in some examples, the tubular member 114 may be expanded via the outward, radial expansion of the expandable member 124. In other words, expanding the expandable member 124 radially outward may result in the outer surface 132 of the expandable member 124 contacting the inner surface 129 of the first layer 120, thereby radially expanding the tubular member 114 outward. For example, FIG. 7 illustrates the outer surface 132 of the expandable member 124 contacting the inner surface 129 of the first layer 120. However, FIG. 7 also illustrates that the inner surface 130 of the expandable member 124 may not contact the outer surface 126 of the second layer 122 of the tubular member 114. Therefore, in some examples, a gap 128 may still exist between the inner surface 130 of the expandable member 124 and the outer surface 126 of the second layer 122. However, this is not intended to be limiting. Rather, in some examples the inner surface 130 of the expandable member 124 may contact the outer surface 126 of the second layer 122 upon expansion of the expandable member 124.

FIG. 7 further illustrates that the tubular member 114 may be designed to expand radially outward while its length foreshortens. For example, it can be appreciated that if the proximal end 136 of the expandable member 124 is fixed (e.g., at fixation points 138) with respect to the manifold 112 and the tubular member 114 is shortened along its longitudinal axis, the expandable member 124 may both shorten and expand radially outward (which may also expand the tubular member 114 radially outward). For example, FIG. 7 shows the length of the tubular member 114 in the expanded configuration as "$L_4$." In some examples, the length $L_3$ of the tubular member 114 in an unexpanded configuration (shown in FIG. 6) may be longer than the length $L_4$ of the tubular member 114 in an expanded configuration (shown in FIG. 7).

FIG. 7 further illustrates the expansion of the expandable member 124 radially outward. As shown in FIG. 7 and discussed above, the proximal end 137 of the tubular member 114 (e.g., the proximal end 137 of the first layer 120)

may extend into and move relative to the manifold 112. It can be further appreciated, therefore, that the manifold 112 may be designed to permit the proximal end 137 of the tubular member 114 to be shifted in a distal-to-proximal direction (as depicted by the arrows in FIG. 7). In other words, it can be appreciated that the manifold 112 may be designed with one or more components (not shown for simplicity purposes) that can "pull" at least a portion of the proximal end 137 of the tubular member 114 such that the proximal end 137 of the tubular member 114 may shift in a distal-to-proximal direction (as depicted by the arrows in FIG. 7). Further, as discussed above, the proximal end 136 of the expandable member 124 may be held stationary via the manifold 112. Consequently, it can be appreciated that if the proximal end 137 of the tubular member 114 is shifted in a distal-to-proximal direction (thereby shortening the tubular member 114) while the proximal end 136 of the expandable member 124 is held stationary, then the expandable member 124 (and, consequently, the tubular member 114) may both foreshorten and expand radially outward.

It should be noted that while the above description discloses a shortening of the tubular member 114 by pulling the proximal end of the first layer 120 in a distal-to-proximal direction, this is not intended to be limiting. Rather, other examples may achieve a similar result by pulling the proximal end of the second layer 122 in a distal-to-proximal direction. Still other examples may pull both the first layer 120 and the second layer 122 in a distal-to-proximal direction to shorten both the tubular member and the expandable member 124.

Figure 8:
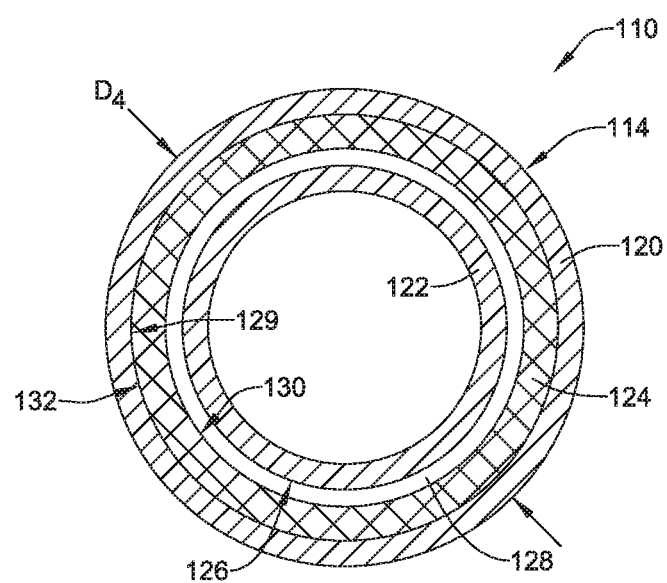
FIG. 8 is a cross-sectional view along line 8-8 of the introducer shown in FIG. 7.

FIG. 8 is a cross-sectional view of the introducer 110 taken along line 8-8 of FIG. 7. FIG. 8 illustrates the tubular member 114 including a second layer 122, first layer 120 and the expandable member 124 disposed within the space 128 between the second layer 122 and first layer 120. It can be appreciated that FIG. 8 may depict the introducer 110 in an expanded configuration. It can be further appreciated that in the expanded configuration, the introducer 110 may include an outer diameter depicted as "D$_4$" in FIG. 8. As discussed above, FIG. 8 illustrates the outer surface 132 of the expandable member 124 contacting the inner surface 129 of the first layer 120. However, FIG. 8 also illustrates that the inner surface 130 of the expandable member 124 may not contact the outer surface 126 of the second layer 122 of the tubular member 114. Therefore, in some examples, a gap 128 may still exist between the inner surface 130 of the expandable member 124 and the outer surface 126 of the second layer 122.

In some examples, introducer 10 and/or introducer 110 may be made from materials such as metals, metal alloys, polymers, ceramics, metal-polymer composites, or other suitable materials, and the like. Some examples of suitable materials may include metallic materials such as stainless steels (e.g. 304v stainless steel or 316L stainless steel), nickel-titanium alloys (e.g., nitinol, such as super elastic or linear elastic nitinol), nickel-chromium alloys, nickel-chromium-iron alloys, cobalt alloys, nickel, titanium, platinum, or alternatively, a polymeric material, such as a high performance polymer, or other suitable materials, and the like. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

In some examples, the introducer 10 and/or introducer 110 may be made from materials such as, for example, a polymeric material, a ceramic, a metal, a metal alloy, a metal-polymer composite, or the like. Examples of suitable polymers may include polyurethane, a polyether-ester such as ARNITEL® available from DSM Engineering Plastics, a polyester such as HYTREL® available from DuPont, a linear low density polyethylene such as REXELL®, a polyamide such as DURETHAN® available from Bayer or CRISTAMID® available from Elf Atochem, an elastomeric polyamide, a block polyamide/ether, a polyether block amide such as PEBA available under the trade name PEBAX®, silicones, polyethylene, Marlex high-density polyethylene, polyetheretherketone (PEEK), polyimide (PI), and polyetherimide (PEI), a liquid crystal polymer (LCP) alone or blended with other materials. In some examples, a suitable polymeric material may have a yield strain of at least 20%, at least 30%, at least 40%, at least 50%, or more. In some examples, the sheath, the membrane, and/or the plurality of corrugations may be made from a material having a low coefficient of friction. In some examples, the sheath, the membrane, and/or the plurality of corrugations may be formed from a fluoropolymer, such as polytetrafluoroethylene (PTFE) or fluorinated ethylene propylene (FEP).

Portions of introducer 10 and/or introducer 110 may be made of, may be doped with, may include a layer of, or otherwise may include a radiopaque material. Radiopaque materials are understood to be materials capable of producing a relatively bright image on a fluoroscopy screen or another imaging technique such as X-ray during a medical procedure. This relatively bright image aids the user of device in determining its location. For example, one or more of the elements described above (i.e., the sheath, the membrane, the medical device, etc.) may include or be formed from a radiopaque material. Suitable materials can include, but are not limited to, bismuth subcarbonate, iodine, gold, platinum, palladium, tantalum, tungsten or tungsten alloy, and the like.

It should be understood that although the above discussion was focused on percutaneous medical procedures within the vasculature of a patient, other examples or methods in accordance with the disclosure can be adapted and configured for use in other parts of the anatomy of a patient. For example, devices and methods in accordance with the disclosure can be adapted for use in the digestive or gastrointestinal tract, such as in the mouth, throat, small and large intestine, colon, rectum, and the like. For another example, devices and methods can be adapted and configured for use within the respiratory tract, such as in the mouth, nose, throat, bronchial passages, nasal passages, lungs, and the like. Similarly, the devices and methods described herein with respect to percutaneous deployment may be used in other types of surgical procedures as appropriate. For example, in some examples, the devices may be deployed in a non-percutaneous procedure. Devices and methods in accordance with the disclosure can also be adapted and configured for other uses within the anatomy.

It should be understood that this disclosure is, in many respects, only illustrative. Changes may be made in details, particularly in matters of shape, size, and arrangement of steps without exceeding the scope of the disclosure. The disclosure's scope is, of course, defined in the language in which the appended claims are expressed.

What is claimed:
1. An introducer sheath, comprising:
a tubular member having a first layer and a second layer;

an expandable member disposed within a gap between the first layer and the second layer;

wherein the tubular member is designed to shift between a first elongated configuration and a second expanded and foreshortened configuration;

wherein shifting the tubular member to the second configuration includes expanding the expandable member, wherein in the second configuration there is no longer a gap between the expanded expandable member and the first layer and a gap is still present between the expanded expandable member and the second layer.

2. The introducer of claim 1, wherein the expandable member is slidable relative to the first layer and second layer of the tubular member.

3. The introducer of claim 1, wherein the expandable member is designed to foreshorten, and wherein foreshortening the expandable member shifts the expandable member from a first configuration to a second expanded configuration.

4. The introducer of claim 1, wherein the first layer of the tubular member is radially outward of the second layer of the tubular member.

5. The introducer of claim 1, wherein the tubular member includes a proximal end, and wherein shifting the proximal end in a proximal direction shifts the expandable member from the first configuration to the second expanded configuration.

6. The introducer of claim 1, wherein the first layer of the tubular member is continuous with the second layer of the tubular member.

7. The introducer of claim 1, wherein the second layer of the tubular member folds back on itself to form the first layer of the tubular member.

8. The introducer of claim 1, wherein the tubular member further comprises a lumen extending therein, and wherein the lumen is positioned radially inward of both the first layer and the second layer.

* * * * *